(12) United States Patent
Tamura

(10) Patent No.: US 9,211,111 B2
(45) Date of Patent: Dec. 15, 2015

(54) DETERMINATION OF SHEAR WAVE CHARACTERISTICS

(75) Inventor: Tadashi Tamura, North Haven, CT (US)

(73) Assignee: HITACHI ALOKA MEDICAL, LTD., Tokyo (JP)

( * ) Notice: Subject to any disclaimer, the term of this patent is extended or adjusted under 35 U.S.C. 154(b) by 170 days.

(21) Appl. No.: 13/603,072

(22) Filed: Sep. 4, 2012

(65) Prior Publication Data

US 2013/0267847 A1 Oct. 10, 2013

Related U.S. Application Data

(60) Provisional application No. 61/620,763, filed on Apr. 5, 2012.

(51) Int. Cl.
*A61B 8/08* (2006.01)

(52) U.S. Cl.
CPC ............... *A61B 8/485* (2013.01); *A61B 8/5207* (2013.01)

(58) Field of Classification Search
None
See application file for complete search history.

(56) References Cited

U.S. PATENT DOCUMENTS

| | | | |
|---|---|---|---|
| 5,606,971 A | 3/1997 | Sarvazyan | |
| 5,810,731 A | 9/1998 | Sarvazyan et al. | |
| 7,252,004 B2 | 8/2007 | Fink et al. | |
| 8,118,744 B2 | 2/2012 | Palmeri et al. | |
| 2008/0249408 A1 | 10/2008 | Palmeri et al. | |
| 2011/0184287 A1* | 7/2011 | McAleavey | 600/438 |
| 2011/0245672 A1* | 10/2011 | Tamura | 600/443 |
| 2012/0108968 A1* | 5/2012 | Freiburger et al. | 600/443 |
| 2013/0131511 A1* | 5/2013 | Peterson et al. | 600/438 |
| 2013/0218012 A1* | 8/2013 | Specht et al. | 600/438 |

FOREIGN PATENT DOCUMENTS

WO 2011126729 A2 10/2003

OTHER PUBLICATIONS

Patent Cooperation Treaty, "PCT International Search Report and PCT Written Opinion of the International Searching Authority", May 14, 2013, for International Application No. PCT/JP2013/059807, 7pgs.

* cited by examiner

*Primary Examiner* — Long V Le
*Assistant Examiner* — Kevin Pontius
(74) *Attorney, Agent, or Firm* — Buckley, Maschoff & Talwalkar LLC

(57) ABSTRACT

A first ultrasound pulse is applied to biological tissue to create shear waves in the biological tissue, an ultrasound pulse is transmitted into the biological tissue, one or more ultrasound signals is received from the biological tissue, and shear waves are detected in the biological tissue based on the received one or more ultrasound signals. At least one propagation property associated with the detected shear waves is determined, and the determined at least one propagation property is displayed.

9 Claims, 17 Drawing Sheets

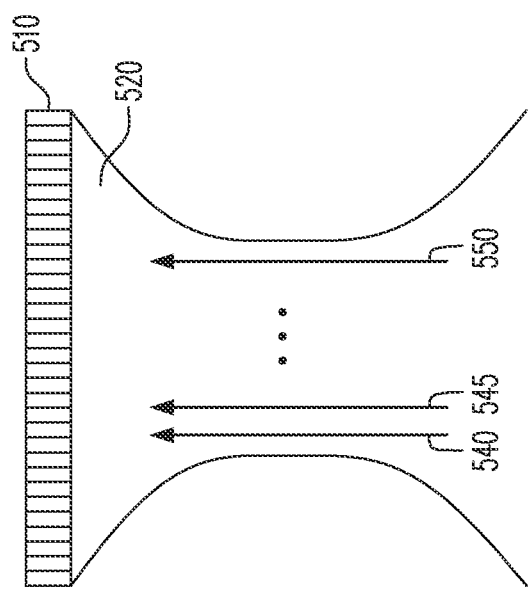

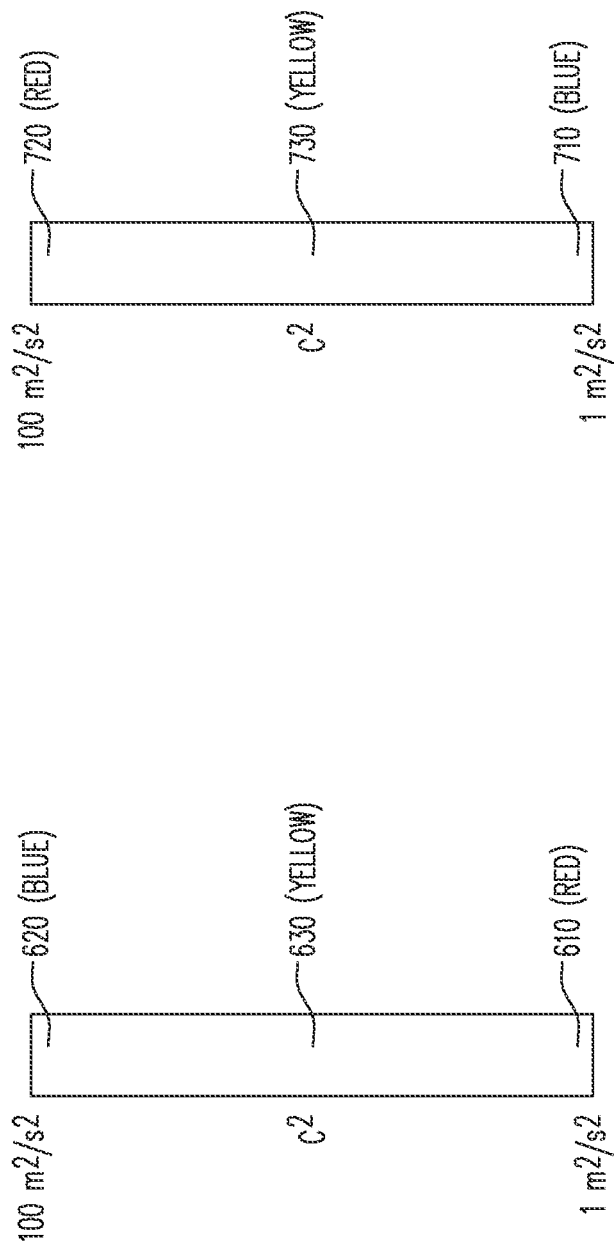

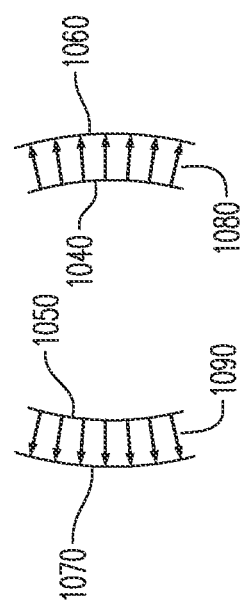
Figure 11
Figure 10

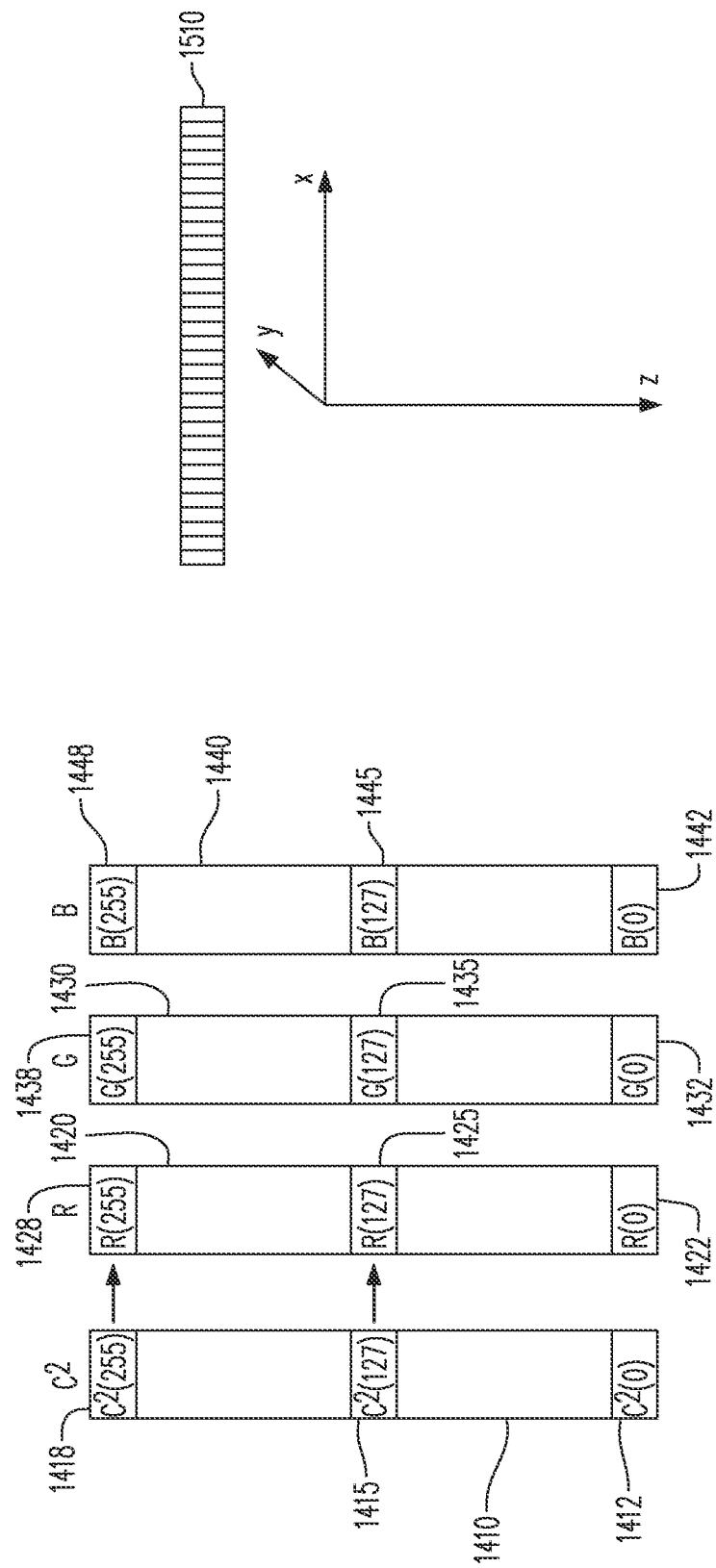

Measurement Points

DETERMINATION OF SHEAR WAVE CHARACTERISTICS

CROSS-REFERENCE TO RELATED APPLICATIONS

The present application claims priority to U.S. Provisional Patent Application Ser. No. 61/620,763, filed on Apr. 5, 2012 and entitled "Method and Apparatus for Ultrasound Imaging", the contents of which are incorporated herein by reference for all purposes.

BACKGROUND

Systems and methods described herein generally relate to the field of ultrasound imaging. More specifically, embodiments described below relate to methods and systems for measuring shear wave velocity squared in tissue.

Pathological conditions may result in soft tissue which is stiffer than would be present under physiological conditions. Physicians therefore use palpation to locate stiff tissue within a body and thereby identify pathological conditions. For example, breast cancers are known to be generally harder than healthy breast tissue and may be detected as a hard lump through palpation.

The square of shear wave propagation velocity in tissue is related to the stiffness (Young's modulus) of tissue by the following equation, $$E = 3\rho \cdot c^2 \quad (1)$$

where c is the propagation velocity of shear wave, E is Young's modulus, and $\rho$ is the tissue density. Therefore, cancers or other pathological conditions may be detected in tissue by measuring the square of propagation velocity of shear waves passing through the tissue.

A shear wave may be created within tissue by applying a strong ultrasound pulse to the tissue. The ultrasound pulse may exhibit a high amplitude and a long duration (e.g., on the order of 100 microseconds). The ultrasound pulse generates an acoustic radiation force which pushes the tissue, thereby causing layers of tissue to slide along the direction of the ultrasound pulse. These sliding (shear) movements of tissue may be considered shear waves, which are of low frequencies (e.g., from 10 to 500 Hz) and may propagate in a direction perpendicular to the direction of the ultrasound pulse.

Since the tissue motion is generally in the axial direction (i.e., the ultrasound pulse direction) the shear waves may be detected using conventional ultrasound Doppler techniques. In this regard, the ultrasound Doppler technique is best suited to detect velocity in the axial direction. Alternately, shear waves may be detected by measuring a tissue displacement caused by the acoustic radiation force.

In order to accurately measure the square of the shear wave propagation velocity, the shear wave needs to be detected multiple positions. A new algorithm may be needed to obtain accurate measurement of the square of the shear wave propagation velocity.

BRIEF DESCRIPTION OF THE DRAWINGS

FIG. 5. A diagram of an ultrasound transmitted beam and multiple ultrasound received beams.

FIG. 6. Color coding of shear wave propagation velocity squared.

FIG. 7. Color coding of shear wave propagation velocity squared.

FIG. 10. A diagram illustrating the propagation of shear waves.

FIG. 11. A diagram illustrating the propagation of shear waves.

FIG. 14. Scale of shear wave velocity squared $c^2$ by color coding bar composed of RGB representation.

FIG. 15. A diagram to show an ultrasound coordinate system with respect to an ultrasound transducer.

DETAILED DESCRIPTION

Embodiments will be described with reference to the accompanying drawing figures wherein like numbers represent like elements throughout. Before embodiments are explained in detail, it is to be understood that embodiments are not limited in their application to the details of the examples set forth in the following description or illustrated in the figures. Other embodiments may be practiced or carried out in a variety of applications and in various ways. Also, it is to be understood that the phraseology and terminology used herein is for the purpose of description and should not be regarded as limiting. The use of "including," "comprising," or "having," and variations thereof herein is meant to encompass the items listed thereafter and equivalents thereof as well as additional items. The terms "mounted," "connected," and "coupled," are used broadly and encompass both direct and indirect mounting, connecting, and coupling. Further, "connected," and "coupled" are not restricted to physical or mechanical connections or couplings.

Figure 1:
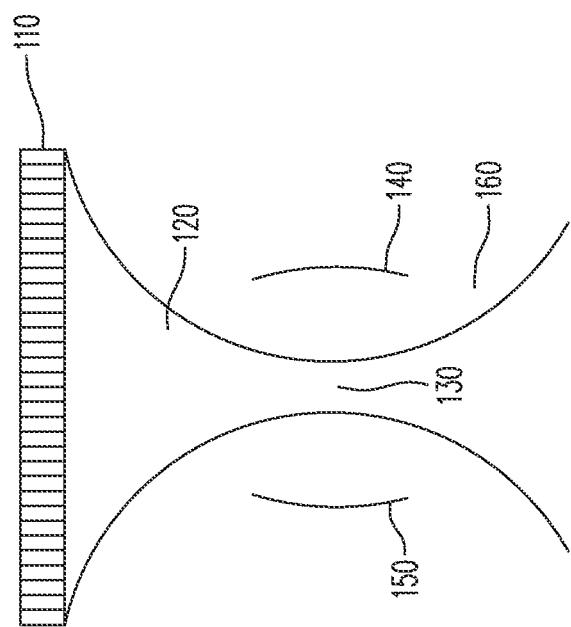
FIG. 1. A diagram of shear wave generation resulting from an acoustic radiation force.

Acoustic radiation force is created by a strong ultrasound pulse 120 as shown in FIG. 1. The ultrasound pulse 120 exhibits a high amplitude as well as a long duration, (e.g., on the order of 100 microseconds). The ultrasound pulse 120 is transmitted from an ultrasound transducer array 110. The ultrasound pulse 120 is focused at a focal point 130 in biological tissue 160, resulting in an acoustic radiation force which pushes the tissue 160 at the focal point 130. The ultrasound pulse 120 may be transmitted multiple times and may be focused at a different focal point for each of multiple transmitted ultrasound pulses.

The tissue 160 is pushed mostly in the axial direction of the ultrasound pulse 120, creating shear waves 140, 150 which may propagate in the lateral direction or directions other than the axial direction (i.e., vertical direction). The square of the propagation velocity of the shear waves 140, 150 depends on the stiffness (i.e., Young's modulus) of the tissue 160. Greater tissue stiffness results in greater shear wave propagation velocity squared as shown in equation 1. Pathological conditions such as cancer may increase tissue stiffness thus these conditions may be diagnosed by determining the propagation velocity squared. For example, the shear wave propagation velocity squared may vary from $1 \, m^2/s^2$ to $100 \, m^2/s^2$, depending on tissue conditions.

Since the shear wave may be characterized by tissue movement (or motion), the shear wave may be detected by the ultrasound Doppler technique (e.g., see U.S. Pat. No. 4,573,477, U.S. Pat. No. 4,622,977, U.S. Pat. No. 4,641,668, U.S. Pat. No. 4,651,742, U.S. Pat. No. 4,651,745, U.S. Pat. No. 4,759,375, U.S. Pat. No. 4,766,905, U.S. Pat. No. 4,768,515, U.S. Pat. No. 4,771,789, U.S. Pat. No. 4,780,837, U.S. Pat. No. 4,799,490, and U.S. Pat. No. 4,961,427). To detect this tissue movement (motion), the ultrasound pulse is transmitted multiple times to the tissue, and the ultrasound is scattered by scatterers in tissue and received by an ultrasound transducer as received ultrasound signals. The received ultrasound signals from the ultrasound array transducers are filtered, amplified, digitized, apotized, and beamformed (i.e. summed) after applying delays and/or phase-rotations for focusing and steering. The order of these processing steps may be interchanged. Received beamformed RF ultrasound signals undergo quadrature demodulation, resulting in complex, Doppler I-Q signals. In a color Doppler technique, the ultrasound is transmitted at a pulse repetition frequency (PRF) and the velocity is detected as the shift in frequency (Doppler shift frequency) in the received ultrasound signal. The received ultrasound is mixed with in-phase (0 degrees) and quadrature (90 degrees) reference signals of the same frequency as the transmitted ultrasound frequency, resulting in complex I-Q Doppler signals.

Generally, the complex I-Q signal is used to derive the Doppler shift frequency because the Doppler shift frequency and the blood velocity have the following relationship $$\Delta f = \frac{2 f_t v \cos\theta}{c_s}, \tag{2}$$

where $\Delta f$ is the Doppler shift frequency, $f_t$ is the transmitted frequency, v is the blood velocity, $\theta$ is the angle between the ultrasound beam direction and the velocity vector, and $c_s$ is the speed of sound. The Doppler shift frequency is thus dependent on the angle between the velocity direction and the ultrasound beam direction and is a measurement that an ultrasound color Doppler system may obtain.

In the case of color Doppler, the number of the sampled signals may be limited to several. Therefore, an auto-correlation technique is usually used to determine the phase differences between the I-Q signals and then to determine the Doppler shift frequency and the velocity as follows. The color Doppler's I-Q signals $z(m)=x(m)+jy(m)$ are used to calculate "auto-correlation" R as shown in the following equation, where $z(m)$ is the complex I-Q Doppler signal, $x(m)$ is the in-phase (real) signal, $y(m)$ is the quadrature phase (imaginary) signal, m indicates the signal number, j is the imaginary unit and * indicates the complex conjugate.

$$R = \Sigma z(m) \cdot z^*(m-1) \tag{3}$$

The real (Re al (R)) and imaginary (Im ag(R)) parts of R are used to obtain the phase $\phi$ as shown in the following equation.

$$\varphi = \tan^{-1} \frac{\text{Image}(R)}{\text{Real}(R)} \tag{4}$$

Since $\tan^{-1}$ usually provides only $-0.5\pi$ to $0.5\pi$, the position of complex value r in the complex coordinate may be also used to derive $\phi$ in the range of $-\pi$ to $\pi$. The phase (i.e., color Doppler phase) $\phi$ is then related to the Doppler shift frequency (i.e., color Doppler shift frequency) as shown in the following equation.

$$\Delta f = \frac{\varphi f_{PRF}}{2\pi} \tag{5}$$

Autocorrelation R between the received complex baseband ultrasound signals is thus obtained to detect tissue velocity or movement.

Tissue movement is detected at multiple lateral points in a field of tissue region by multiple ultrasound beams (for example, 540, 545, 550 in FIG. 5) in order to monitor movement. This movement reflects action of the shear wave at those multiple lateral points (or multiple ultrasound beams). Consequently, the lateral propagation velocity of the shear wave may be determined from the detected tissue movement.

Figure 13:
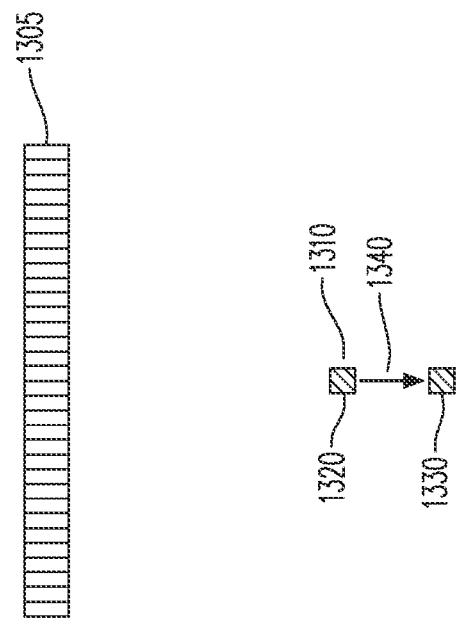
FIG. 13. A diagram to illustrate tissue displacement caused by an acoustic radiation force.

Alternately, the shear wave may be detected by measuring tissue displacement caused by acoustic radiation force which is in turn caused by a strong ultrasound pulse as shown in FIG. 13. Tissue 1310 is positioned at a position 1320 before the acoustic radiation is applied and then is moved to a position 1330 after the acoustic radiation force was applied. To measure tissue displacement caused by the strong ultrasound pulse, ultrasound pulses are transmitted to tissue from an ultrasound transducer 1305 and then the ultrasound pulses are scattered from scatterers in tissue and returned to the transducer 1305 and received by the transducer 1305 as received ultrasound signals. The ultrasound pulses are focused at a depth in order to increase a signal-to-noise ratio of the resulting received ultrasound signals in comparison to unfocused ultrasound pulses. Using correlation of the received ultrasound signals from tissue the displacement 1340 (from the position 1320 to the position 1330) of the tissue 1310 due to the acoustic radiation force may be obtained and the tissue 1310 may be tracked thereafter. The ultrasound pulses may thereby track shear waves after shear waves are created by acoustic radiation force.

Ultrasound signals resulting from the first ultrasound pulse and received from the tissue 1310 before acoustic radiation force is applied are cross-correlated with received ultrasound signals resulting from the second ultrasound pulse after the acoustic radiation force is applied in order to find the best match between the received ultrasound signals. The best match may be found by finding a maximum correlation value to track the tissue and its displacement due to the acoustic radiation force. Therefore, when tissue displacement is observed or measured, a shear wave is detected. The displacement and tissue velocity may be related in that the displacement is a time integral $\int v_s dt$ of tissue velocity $v_s$. Therefore, the tissue displacement may be obtained by calculating the time integral of color Doppler velocity. Received ultrasound signals may be RF (Radio Frequency), IF (Intermediate Frequency) or baseband signals after demodulation. Alternately, the displacement may be further differentiated to obtain tissue strain, which may be then used to detect the square of shear wave propagation velocity.

Cross correlation $CC(t, \tau)$ of signals in the previous paragraphs may be mathematically expressed as follows, $$CC(t,\tau) = \int_t^{t+W} S_1(t') S_2(t'-\tau) dt' \quad (6)$$

where $CC(t,\tau)$: cross correlation; $S_1(t')$: received signal from the first ultrasound transmission; $S_2(t'-\tau)$: received ultrasound signal from the second ultrasound transmission; W: window length; t: time, t': time; $\tau$: time displacement. Time displacement value $\tau$, which makes the maximum cross correlation (or the best match), determines the tissue displacement. Interpolation of signals using an interpolation function (e.g., cubic-spline) may be performed before cross correlation to increase spatial resolution.

The cross correlation may be replaced by the sum of absolute differences (SAD), the sum of square differences (SSD), the sum of absolute cubic differences (SCD), or the sum of absolute power differences (SPD) as follows.

$$SAD[l, k] = \sum_{n=0}^{N} |S_1[l+n] - S_2[l+n-k]| \quad (7)$$

$$SSD[l, k] = \sum_{n=0}^{N} (S_1[l+n] - S_2[l+n-k])^2 \quad (8)$$

$$SCD[l, k] = \sum_{n=0}^{N} |S_1[l+n] - S_2[l+n-k]|^3 \quad (9)$$

$$SPD[l, k] = \sum_{n=0}^{N} |S_1[l+n] - S_2[l+n-k]|^p \quad (10)$$

$S_1$ is the received ultrasound signal from the first ultrasound transmission before displacement, $S_2$ is the received ultrasound signal from the second ultrasound transmission after displacement. N: the number of signals in the signal window. k: window displacement by the number of signals and equivalent of $\tau$. l: the position of the window. p is a real number. For SAD, SSD, SCD and SPD, the tissue displacement is determined based on the value of k that makes the minimum (or best match) of each of the SAD, SSD, SCD and SPD.

Figure 9:
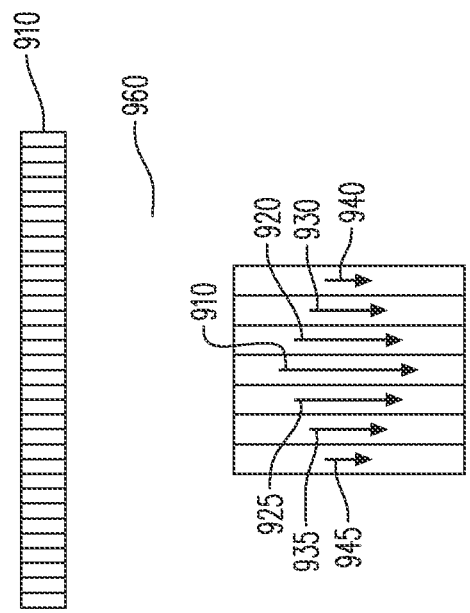
FIG. 9. A diagram illustrating sliding movements of shear waves.
Figure 8:
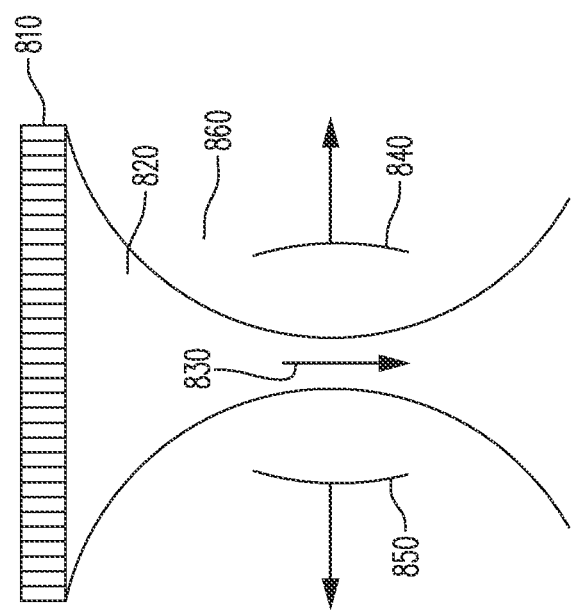
FIG. 8. A diagram illustrating generation of shear waves by acoustic radiation forces and the propagation of shear waves.

FIGS. 8 and 9 illustrate shear wave generation and detection in detail. A strong ultrasound pulse 820 is applied to tissue 860, 960 from an ultrasound transducer 810, 910 once or more times to increase the amplitude of shear waves which are caused by acoustic radiation forces resulting from the ultrasound pulse. Shear waves attenuate very quickly in tissue and thus a greater amplitude results in a greater propagation distance. One or multiple ultrasound pulses may be focused at one focal point or different focal points. The ultrasound pulse creates acoustic radiation forces which push a layer of tissue, resulting in tissue movement 830, 910 mostly in the axial (vertical) direction as illustrated in FIG. 9. The tissue layer movement 910 causes adjacent tissue layer movements 920, 925 mostly in the axial direction. The tissue layer movements 920, 925 then in turn cause next tissue layer movements 930, 935 which then cause adjacent tissue layer movements 940, 945. This succession of tissue movements represents a propagation of shear waves 840, 850 in the lateral (horizontal) direction as shown in FIG. 8. Since the tissue movements (or motions) caused by acoustic radiation forces are mostly in the axial direction, the motion may be detected by the color Doppler technique, which is sensitive to motions in the axial direction.

For example, the color Doppler technique transmits and receives several ultrasound pulses, determines phase differences between the received ultrasound signals, and calculates a velocity of tissue or blood using the autocorrelation technique as previously discussed and known in the art. Variance and power of color Doppler signals may be also calculated in addition to the velocity. As in the conventional display of moving tissue or blood, one of these parameters may be used to display shear waves as shown in FIGS. 10, 11. It will be assumed that shear waves 1040 (1140), 1050 (1150) are determined in a color Doppler frame representing a certain time and shear waves 1060 (1160), 1070 (1170) are determined at a next moment or in a next frame. More image frames of shear waves may be obtained to track the shear waves and to create a movie of shear wave propagation. In alternate embodiments, tissue displacement due to acoustic radiation forces may be detected.

FIGS. 10 and 11 depict shear wave propagation at two points in time. Local shear wave propagation velocity squared, as illustrated by arrows 1080, 1090, may be derived by correlating two images of shear waves at two points in time. More image frames of shear waves may be used to track the propagation of shear waves in more image areas in order to present local shear wave propagation velocity squared in a two-dimensional image as described below.

Correlation coefficient (CCV) between a first frame signal $S^1$ and the second frame signal $S^2$ may be obtained as speckle tracking as follows, $$CCV(S^1, S^2) = \frac{\sum_{x=1}^{m} \sum_{z=1}^{n} (S^1_{x,z} - \overline{S^1})(S^2_{x+X, z+Z} - \overline{S^2})}{\sqrt{\sum_{x=1}^{m} \sum_{z=1}^{n} (S^1_{x,z} - \overline{S^1})^2 \cdot \sum_{x=1}^{m} \sum_{z=1}^{n} (S^2_{x+X, z+Z} - \overline{S^2})^2}} \quad (11)$$

where $S^1_{x,z}$ is the ultrasound signal at x, z of the first frame, $S^2_{x+X, z+Z}$ is the ultrasound signal at x+X, z+Z of the second frame, $\overline{S^1}$ is mean signal value in the window of the first frame signal, $\overline{S^2}$ is mean signal value in the window of the second frame signal. The coordinate system (x,y,z) is shown with respect to an ultrasound transducer 1510 in FIG. 15. The elevational axis y is perpendicular to the paper of FIG. 15 although it is shown slightly different for illustration purposes.

The displacement X, Z, that yields the maximum correlation coefficient is determined and then the square of the displacement is determined and divided by the square of time between the first and second frame signals to obtain the square of shear wave propagation velocity.

Similar to the 1D case, the correlation coefficient may be replaced by the sum of absolute differences (SAD), the sum of square differences (SSD), the sum of absolute cubic differences (SCD) and the sum of absolute power differences (SPD) as follows.

$$SAD(S^1, S^2, X, Z) = \sum_{x=1}^{m} \sum_{z=1}^{n} |S_{x,z}^1 - S_{x+X,z+Z}^2| \qquad (12)$$

$$SSD(S^1, S^2, X, Z) = \sum_{x=1}^{m} \sum_{z=1}^{n} (S_{x,z}^1 - S_{x+X,z+Z}^2)^2 \qquad (13)$$

$$SCD(S^1, S^2, X, Z) = \sum_{x=1}^{m} \sum_{z=1}^{n} |S_{x,z}^1 - S_{x+X,z+Z}^2|^3 \qquad (14)$$

$$SPD(S^1, S^2, X, Z) = \sum_{x=1}^{m} \sum_{z=1}^{n} |S_{x,z}^1 - S_{x+X,z+Z}^2|^p \qquad (15)$$

p is a real number; m and n are integers. The 2D speckle tracking may be approximated by a 1D speckle tracking to obtain the shear wave propagation velocity squared. The mathematical expression will be similar to that used in the displacement measurement.

Alternately, a shear wave equation (16) may be used to derive the shear wave propagation velocity squared as follows, $$\rho \frac{\partial^2 u_i}{\partial t^2} = \mu \left( \frac{\partial^2 u_i}{\partial x^2} + \frac{\partial^2 u_i}{\partial y^2} + \frac{\partial^2 u_i}{\partial z^2} \right) \qquad (16)$$

where i=x, y, z, $\rho$ is tissue density, $\mu$ is the shear modulus, $u_i$ is the displacement vector, x is lateral coordinate, y is elevational coordinate and z is axial coordinate as shown in FIG. 15. For incompressible materials, the Young's modulus E and the shear modulus $\mu$ have the following relationship.

$$E = 3\mu \qquad (17)$$

Therefore, the shear wave propagation velocity squared may be obtained as a ratio of the shear modulus to the density as the following equation.

$$c^2 = \frac{\mu}{\rho} \qquad (18)$$

One of the displacement components $u_z$ in equation 16 may be determined by cross-correlation as previously discussed. By combining z component of equation 16 and equation 18, the shear wave propagation velocity squared is obtained as follows, $$c^2 = \frac{\frac{\partial^2 u_z}{\partial t^2}}{\frac{\partial^2 u_z}{\partial x^2} + \frac{\partial^2 u_z}{\partial y^2} + \frac{\partial^2 u_z}{\partial z^2}}. \qquad (19)$$

Therefore, the shear wave propagation velocity squared is obtained as the ratio between the temporal second-order derivative of the displacement and the spatial second-order derivatives of the displacement. Since the spatial derivative of the displacement in elevational direction $$\frac{\partial^2 u_z}{\partial y^2}$$

may be considered negligible compared with the other spatial derivatives, the shear wave propagation velocity squared may be obtained from the other measurement values.

It is desirable to monitor and to track the shear wave frequently, meaning at a fast rate or frame rate. To speed up the frame rate, a wide, focused ultrasound pulse 520 may be transmitted and multiple ultrasound signals 540, 545, 550 may be simultaneously received as shown in FIG. 5. The received ultrasound beams are used as described previously to detect shear waves and to derive shear wave propagation properties (i.e., velocity squared) therefrom. The focused transmit ultrasound beam 520 may be particularly suitable for maintaining a good signal-to-noise ratio of resulting received ultrasound beams during the detection of shear waves.

Figure 4:
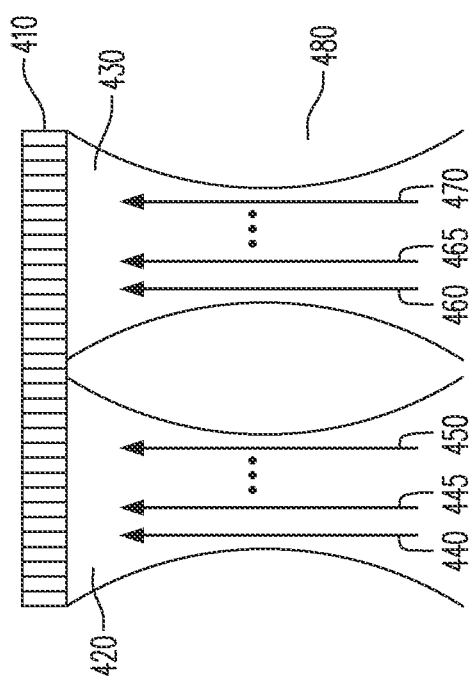
FIG. 4. A diagram of multiple ultrasound transmitted/received beams.

In some embodiments, multiple ultrasound beams (pulses) are simultaneously applied and transmitted to the tissue field and multiple ultrasound beams (pulses) per transmitted ultrasound pulse are received to increase the frame rate, as shown in FIG. 4. In FIG. 4, ultrasound pulses 420, 430 are simultaneously transmitted to biological tissue 480 from an ultrasound transducer array 410. For each transmitted ultrasound pulse 420, 430, multiple ultrasound receive signals 440, 445, 465, 460, 465, 470 are simultaneously received. The multiple ultrasound pulses may be transmitted simultaneously or at substantially simultaneous times. The multiple ultrasound pulses may be simultaneously transmitted. Or a second ultrasound pulse may be transmitted after a first ultrasound pulse is transmitted and before the first ultrasound pulse returns to the ultrasound transducer from a deepest depth of an ultrasound field. This transmission method increases the frame rate.

FIG. 4 shows an example of two simultaneous transmitted ultrasound pulses but more than two transmitted ultrasound pulses may be also used. In some embodiments, coded ultrasound waveforms may be transmitted for better separation of simultaneous multiple ultrasound signals. For example, chirp codes, Barker codes, Golay codes or Hadamard codes may be used for better separation of ultrasound pulses. Again, the received signals are analyzed using the methods previously described to determine tissue movement at multiple points, and shear wave propagation properties are derived therefrom.

An image of a shear wave can be created based on the motion (or velocity) detected at multiple points in the imaging field. Subsequent transmit/receive sequences of ultrasound may create multiple images of the shear wave at multiple points in time. Correlation between the images of the shear wave is then calculated to obtain the shear wave propagation velocity squared as previously discussed. Alternately, tissue displacement caused by acoustic radiation force is determined and the shear wave propagation velocity squared is calculated as the ratio between the temporal second-order derivative of the displacement and the spatial second-order derivatives of the displacement.

In some embodiments, the propagation velocity squared ($c^2$) of the detected shear wave may be displayed. Advantageously, the shear wave propagation velocity squared ($c^2$) may be more closely related than the propagation velocity (c) to the Young's modulus or the shear modulus as shown in equation 1. Therefore the propagation velocity squared ($c^2$) may provide an efficient proxy for the actual stiffness. In some embodiments, the propagation velocity squared ($c^2$) may be multiplied by three and then displayed. If tissue density is close to 1 g/cm$^3$, this number (i.e., $3c^2$) may be close to the actual Young's modulus. In some embodiments, a product ($bc^2$) of any real number (b) and the propagation velocity squared ($c^2$) may be displayed. Determinations of actual stiffness are difficult and error-prone because the density of the tissue is unknown and must be estimated.

A color coding technique, a grayscale technique, or a graphical coding technique may be employed to present a shear wave propagation property (i.e., velocity squared $c^2$) to a user. In some embodiments, a propagation velocity squared ($c^2$) of shear waves within tissue is displayed in a two-dimensional color image. Graphical-coding and/or two-dimensional images may also be used to represent the propagation velocity squared $c^2$ in some embodiments.

A low value of shear wave propagation velocity squared $c^2$ may be coded using a red color while a high value of $c^2$ may be coded using a blue color. For example, FIG. 6 illustrates a legend indicating that a red-colored tissue area includes shear waves associated with low $c^2$ values (e.g., 1 $m^2/s^2$) and that a blue-colored tissue area includes shear waves associated with high $c^2$ values (e.g., 100 $m^2/s^2$). Embodiments are not limited to color-based coding. Images of shear wave propagation properties within tissue may be coded using grayscale or any combination of graphical patterns (e.g., vertical lines, horizontal lines, cross-hatching, dot patterns of different densities, etc.) and colors.

After determining the propagation velocity squared ($c^2$), $c^2$ may be coded linearly with respect to the color wavelength as shown in FIG. 6. For example, if $c^2$ within a tissue area is determined to be 50 $m^2/s^2$, the tissue area may be displayed using a yellow color 630.

Alternately, color-coding of the shear wave propagation velocity squared ($c^2$) may be defined as shown in FIG. 7. Tissue areas associated with low values of the shear wave propagation velocity squared may be displayed as blue 710 while areas associated with high values of the velocity squared may be displayed as red 720. Different color-coding methods may be also used to represent the shear wave propagation velocity squared ($c^2$). For example, color coding may be based on hue, brightness, and other color characteristics. The color-coded scale may represent different maximums and minimums of the shear wave propagation velocity squared than shown in FIG. 6, 7. In this regard, the velocity squared maximum of 100 $m^2/s^2$ and velocity squared minimum of 1 $m^2/s^2$ in FIGS. 6 and 7 are only for the illustration purposes and do not limit the scope of the claims. Other values may represent the maximum or minimum values of the coding scale.

Color coding based on Red, Green and Blue (RGB) values may be used to represent the propagation velocity c or velocity squared ($c^2$) of shear waves as shown in FIG. 14. In this example (FIG. 14), the propagation velocity squared ($c^2$) of a shear wave within tissue is represented according to a color coding bar 1410 which is based on RGB values 1420, 1430 and 1440. The shear wave propagation velocity squared has 256 possible values in this example, as represented 256 colors in the color coding bar 1410. The smallest velocity squared $c^2(0)$ 1412 is represented by a color composed of a combination of R(0) 1422, G(0) 1432 and B(0) 1442. The middle velocity squared $c^2(127)$ 1415 is represented by a color composed of a combination of R(127) 1425, G(127) 1435 and B(127) 1445. The highest velocity squared $c^2(255)$ 1418 is represented by a color composed of a combination of R(255) 1428, G(255) 1438 and B(255) 1448. In this example, R(255) only indicates a Red color associated with the red index 255 and does not necessarily indicate a Red color value of 255, which is the brightest Red color. Likewise, G(255) indicates a Green color associated with the green index 255 and B(255) indicates a Blue color associated with the blue index 255.

Alternately, Red, Green, Blue and Yellow may be used to define a color coding bar. Alternately, a Hue-based color coding bar may be used.

Figure 12:
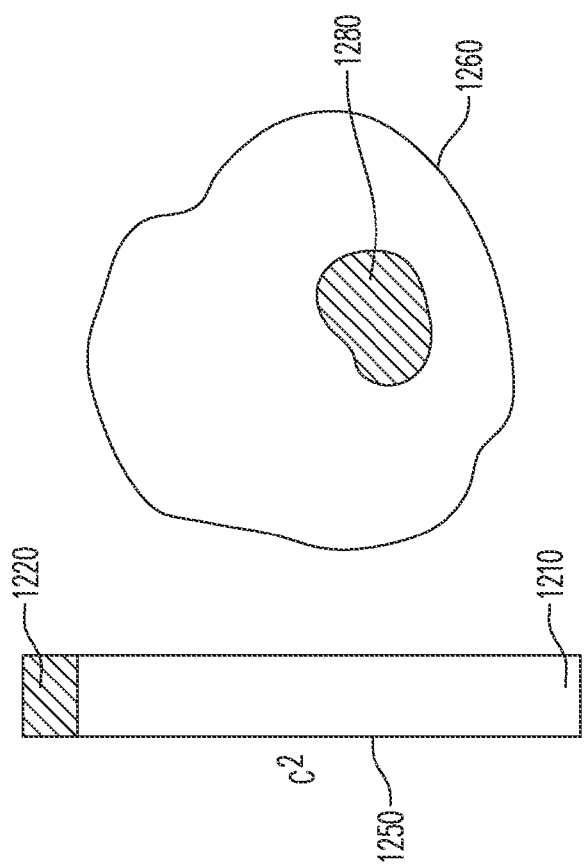
FIG. 12. An example of a color-coded image of shear wave propagation velocity squared in tissue.

FIG. 12 represents an example of a color-coded image 1260 displaying a shear wave propagation velocity squared $c^2$ within human soft tissue (e.g. breast). A color coding scale 1250 is illustrated, in which a color code 1210 (i.e., representing a red color although displayed as white in this black/white document) represents a low shear wave propagation velocity squared value and a color code 1220 (i.e., representing a blue color although displayed as hatched in this black/white document) represents a higher shear wave propagation velocity squared value.

Based on the coding scale 1250, it can be seen that the color coded image 1260 includes an area 1280 of high propagation velocity squared $c^2$. Since the shear wave propagation velocity squared $c^2$ is proportional to the Young's modulus, the tissue area corresponding to area 1280 is likely to be hard. Since a tumor is generally hard, image 1260 may indicate pathological conditions.

The color-coding method provides efficient distinction between an area including shear waves having a high propagation velocity squared value and other areas including shear waves having a low propagation velocity squared value. The color coding method therefore allows efficient identification of hard tissue areas within soft tissue areas. An image displaying shear wave propagation velocity squared may be combined (e.g., superimposed) with a regular image of ultrasound, e.g. B-mode image, or a combined B-mode image and color Doppler image and/or spectral Doppler image. Alternately, the shear wave propagation velocity squared may be displayed numerically. In some embodiments, the shear wave propagation velocity squared may be displayed in gray scale or based on other graphic coding methods such as using patterns rather than colors. For example, low values of square of the shear wave propagation velocity may be displayed in black or dark gray while high values of shear wave propagation velocity squared may be displayed in light gray or white using a grayscale coding method.

In some embodiments, a first ultrasound pulse is applied to biological tissue to create shear waves. A second ultrasound pulse is transmitted to the biological tissue. One or more ultrasound signals generated in the biological tissue are received from the biological tissue. The shear waves in the biological tissue are detected based on the received one or more ultrasound signals. A time to peak displacement of the shear waves at each of multiple positions in the biological tissue is determined. A square of shear wave propagation velocity is determined based on the determined time to peak displacement of the shear waves at each of the multiple positions.

In some embodiments, a first ultrasound pulse is applied to biological tissue to create shear waves. A second ultrasound pulse is transmitted to the biological tissue. A first ultrasound signal generated in the biological tissue in response to the second ultrasound pulse is received from the biological tissue. A third ultrasound pulse is transmitted to the biological tissue. A second ultrasound signal generated in the biological tissue in response to the third ultrasound pulse is received from the biological tissue. The shear waves in the biological tissue are detected based on the received first and second ultrasound signals. A time to peak displacement of the shear waves at each of multiple positions in the biological tissue is determined. A square of shear wave propagation velocity is determined based on the determined time to peak displacement of the shear waves at each of the multiple positions.

Figure 19:
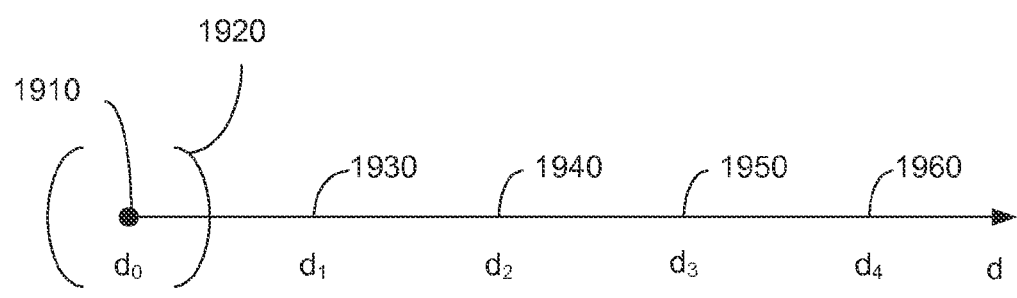
FIG. 19. A diagram illustrating an origin of shear waves and measurement points.

In some embodiments, the square of shear wave propagation velocity may be obtained by detecting a shear wave at only 2 points. FIG. 19 shows the origin of a shear wave 1910. According to some embodiments, the time of flight (t) of a shear wave between the 2 points 1930 and 1940 is determined. For example, the time of flight (t) may be determined by measuring an amount of time which elapses between peak tissue displacement at point 1930 and peak tissue displacement at point 1940. Also the distance (d) between the two points 1930 and 1940 may be determined. The square of shear wave propagation velocity ($c^2$) may then be determined by dividing the distance squared $d^2$ by the time squared $t^2$ as follows, $$c^2 = \frac{d^2}{t^2}. \tag{20}$$

In some embodiments, the square of shear wave propagation velocity may be accurately obtained by detecting a shear wave at multiple points and determining the time of flight for a distance between two of the points. FIG. 19 shows the origin of a shear wave 1910 and multiple points 1910, 1930, 1940, 1950 and 1960 as described above. A shear wave 1920 may be created by strong transmit ultrasound pulses at the origin of shear wave 1910 shown in FIG. 19.

Cross-correlation, SAD, SSD, SCD or SPD between a first received ultrasound signal and a second received ultrasound signal may be used to track tissue displacement as previously discussed. The first received ultrasound signal may be acquired as a reference signal before the shear waves are created while the second received ultrasound signal may be acquired after the shear waves are created. The tissue displacement is a distance corresponding to a time displacement which maximizes cross-correlation $CC(t,\tau)$ in equation (6). For SAD, SSD, SCD or SPD in equations (7), (8), (9), and (10), a distance corresponding to a window displacement which makes the SAD, SSD, SCD or SPD minimum is the tissue displacement as previously described. In some embodiments, the reference signal may be acquired after the shear waves are created. The shear wave may be also detected and monitored at the origin of shear wave 1910. The distances from the origin of shear wave to each measurement point are denoted $d_0$, $d_1$, $d_2$, $d_3$ and $d_4$ as shown in FIG. 19. For example, $d_0$ is zero.

In some embodiments, a color Doppler velocity, a color Doppler shift frequency or a color Doppler phase (as shown in equations 2, 3, 4 and 5) may be calculated based on the I-Q signals of the received ultrasound signals in order to track tissue displacement and thus to determine the time to peak displacement as previously discussed. A time integral of the color Doppler velocity (or color Doppler shift frequency, color Doppler phase) yields the tissue displacement as previously described. The angle θ in equation 2 may be considered zero (0) degrees in this case.

Figure 16:
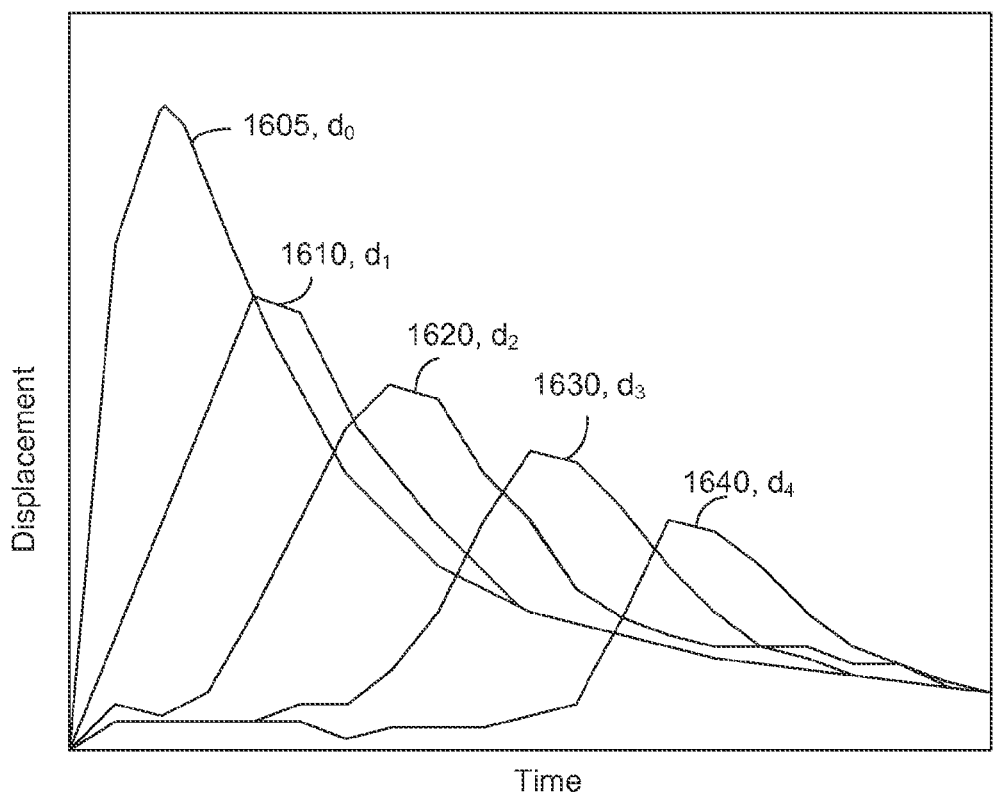
FIG. 16. A diagram illustrating displacement changes over time at multiple positions.
Figure 17:
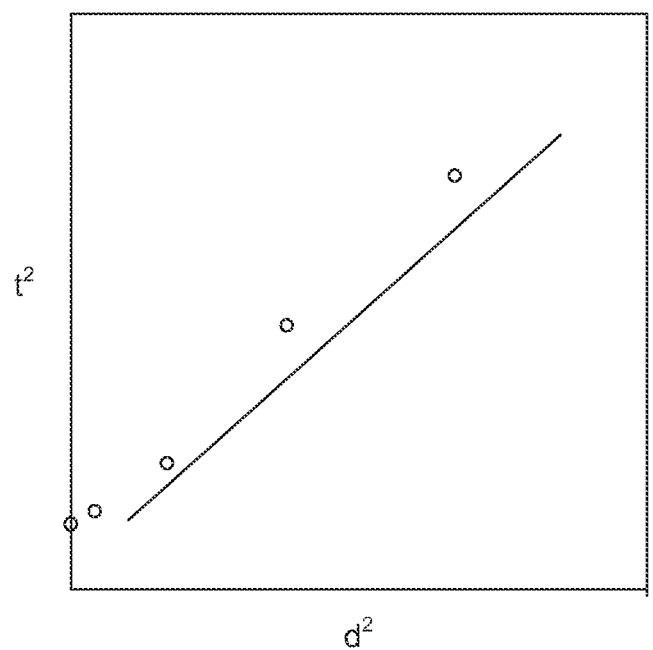
FIG. 17. A diagram of the square of time to peak displacement plotted against the square of distance from the origin of shear waves in a homogenous area.

FIG. 16 shows the tissue displacement changes (Y-axis) over time (X-axis) due to the shear wave observed at multiple points (i.e. each depicted by a respectively-labeled curve) in the tissue. Times to the peak displacement from the origin of the shear wave to the multiple points are shown in FIG. 16. The distances (i.e., $d_0$, $d_1$, $d_2$, $d_3$, $d_4$) from the origin of the shear wave to the multiple points are squared ($d^2$, X-axis) and plotted against the square of the time to the peak displacement ($t^2$, Y-axis) as shown in FIG. 17 in order to measure the square of the shear wave propagation velocity. In this regard, the square of the shear wave propagation velocity is directly related to the tissue stiffness or Young's modulus via the tissue density as shown in equation 1. A regression line is obtained between the distance squared and the time squared as shown in FIG. 17 in order to increase the measurement accuracy.

The regression line is a line to closely relate variables X and Y by minimizing errors. Variable X ($X_i$: actual shear data samples) and variable Y ($Y_i$: actual strain data samples) at a given image point (pixel) are assumed related by a regression line; e.g.

$$Y = aX + b \tag{21}$$

and a and b are obtained to minimize the sum of errors (e.g., square errors) as follows, $$\Sigma(Y_i - aX_i - b)^2 \tag{22}$$

where an error is a difference between the estimated Y value $Y_{est}$ by the regression line for a given $X_i$ using the regression line and the actual data sample $Y_i$ as follows, $$Y_{est} = aX_i + b \tag{23}$$

$$\text{Error} = Y_i - Y_{est} \tag{24}$$

The square of shear wave propagation velocity can be determined by detecting the shear wave at only 2 points and by measuring the time (t) between the 2 points which are separated by a known distance d. However, using more than 2 points may increase the measurement accuracy if the tissue is homogeneous and exhibits the same shear wave property (i.e., the square of shear wave propagation velocity) throughout. Therefore, a regression line may be obtained between the distance squared $d^2$ and the time squared $t^2$ and used to determine the square of shear wave propagation velocity $c^2$. The slope (or the inverse of slope) of the regression line may indicate the square of shear wave propagation velocity.

However, even at the shear wave origin 1910, the time to peak displacement may not be exactly 0 from the onset of shear wave creation, resulting in an offset time. Therefore, the regression line may not intersect the graph origin (0, 0) as shown in FIG. 17, resulting in an offset from the graph origin (0, 0). Therefore, the regression line may conform to the following equation, assuming $t^2$ as the Y-axis and $d^2$ as the X-axis.

$$Y = aX + b \tag{25}$$

or $$t^2 = ad^2 + b \tag{26}$$

Consequently, the inverse 1/a of the regression line slope may indicate the square of the shear wave propagation velocity.

In some embodiments, the time to peak displacement at the shear wave origin may be subtracted from the time to peak displacement at each of multiple positions before calculating the square of the time to peak displacement at each of multiple positions. This process may eliminate the offset (b) of the regression line at the origin as discussed in the previous section. This process may improve the measurement accuracy.

Figure 18:
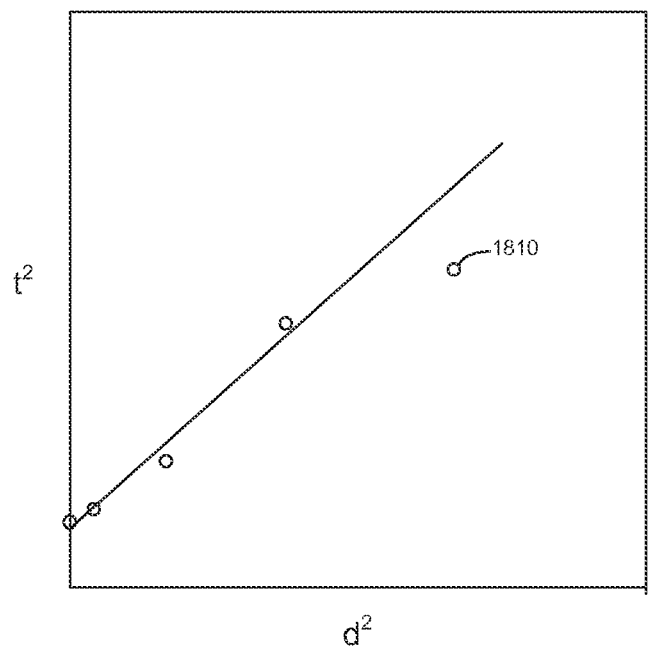
FIG. 18. A diagram of the square of time to peak displacement plotted against the square of distance from the origin of shear waves in a heterogeneous area.

Tissue may be heterogeneous and may exhibit various stiffnesses and various values for the square of the shear wave propagation velocity from one point to another. FIG. 18 shows such a case of heterogeneous tissue. A correlation coefficient is calculated between the time squared and the distance squared.

The correlation coefficient r between data samples $X_i$ and data samples $Y_i$ is obtained as follows, $$r = \frac{\sum_{i=1}^{n}(X_i - \overline{X})(Y_i - \overline{Y})}{\sqrt{\sum_{i=1}^{n}(X_i - \overline{X})^2}\sqrt{\sum_{i=1}^{n}(Y_i - \overline{Y})^2}} \quad (27)$$

where $\overline{X}$ and $\overline{Y}$ are mean of $X_i$ and $Y_i$, respectively.

If the correlation coefficient is lower than a preset threshold value, a regression line is not obtained between the data used for the calculation of correlation coefficient. A regression line is obtained only for data which is associated with a suitably high correlation coefficient. In FIG. 18, one data value 1810 on the right side indicates a different stiffness and a different square of shear wave propagation velocity than the four data values on the left side, resulting in a lower correlation coefficient than that represented in FIG. 17. Therefore, the one data value 1810 on the right side is excluded and only the four data values on the left side are used to obtain a regression line and a correlation coefficient. Improved measurement of the square of shear wave propagation velocity is thereby achieved in some embodiments.

Figure 20:
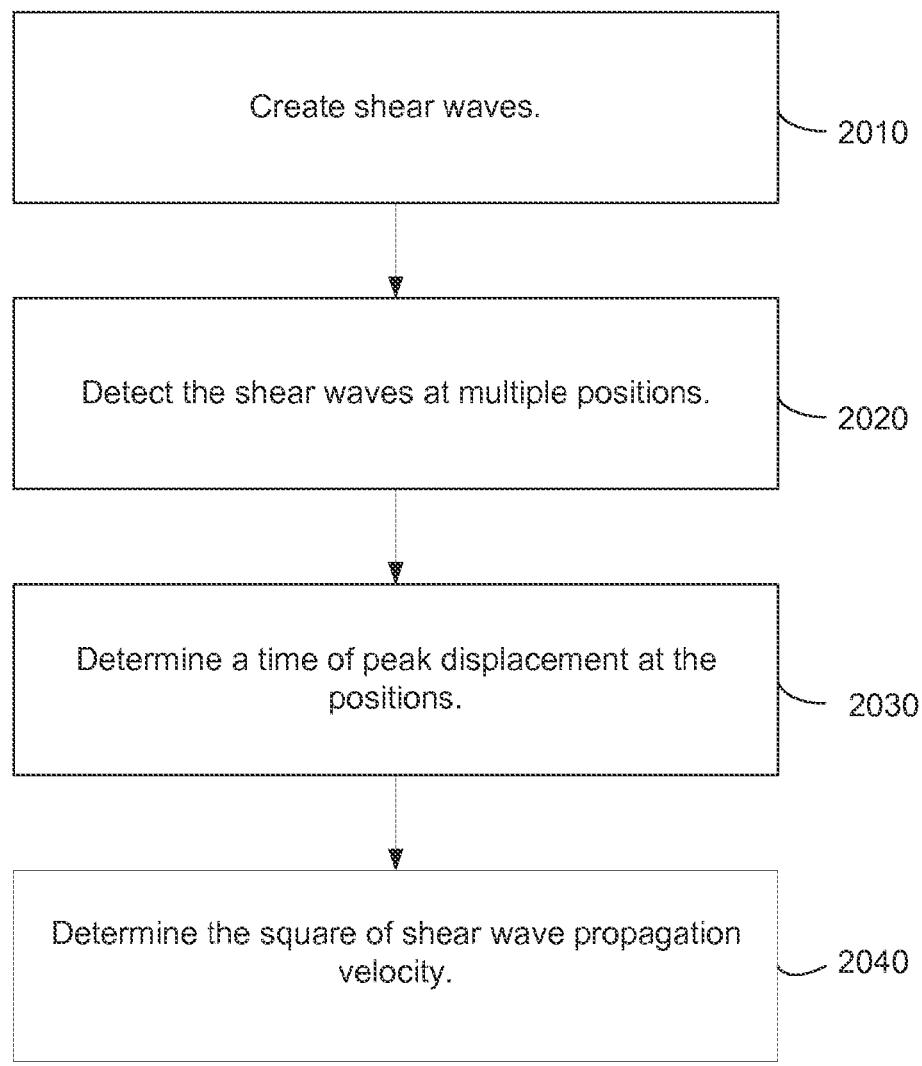
FIG. 20. Flow chart of a process according to some embodiments.

FIG. 20 is a flow chart of a process according to some embodiments. Shear waves are created at 2010. The shear waves are detected at multiple positions at 2020. A time to peak displacement is determined for each of the positions at 2030. The square of shear wave propagation is determined at 2040 based on the determined times to peak displacement.

Figure 21:
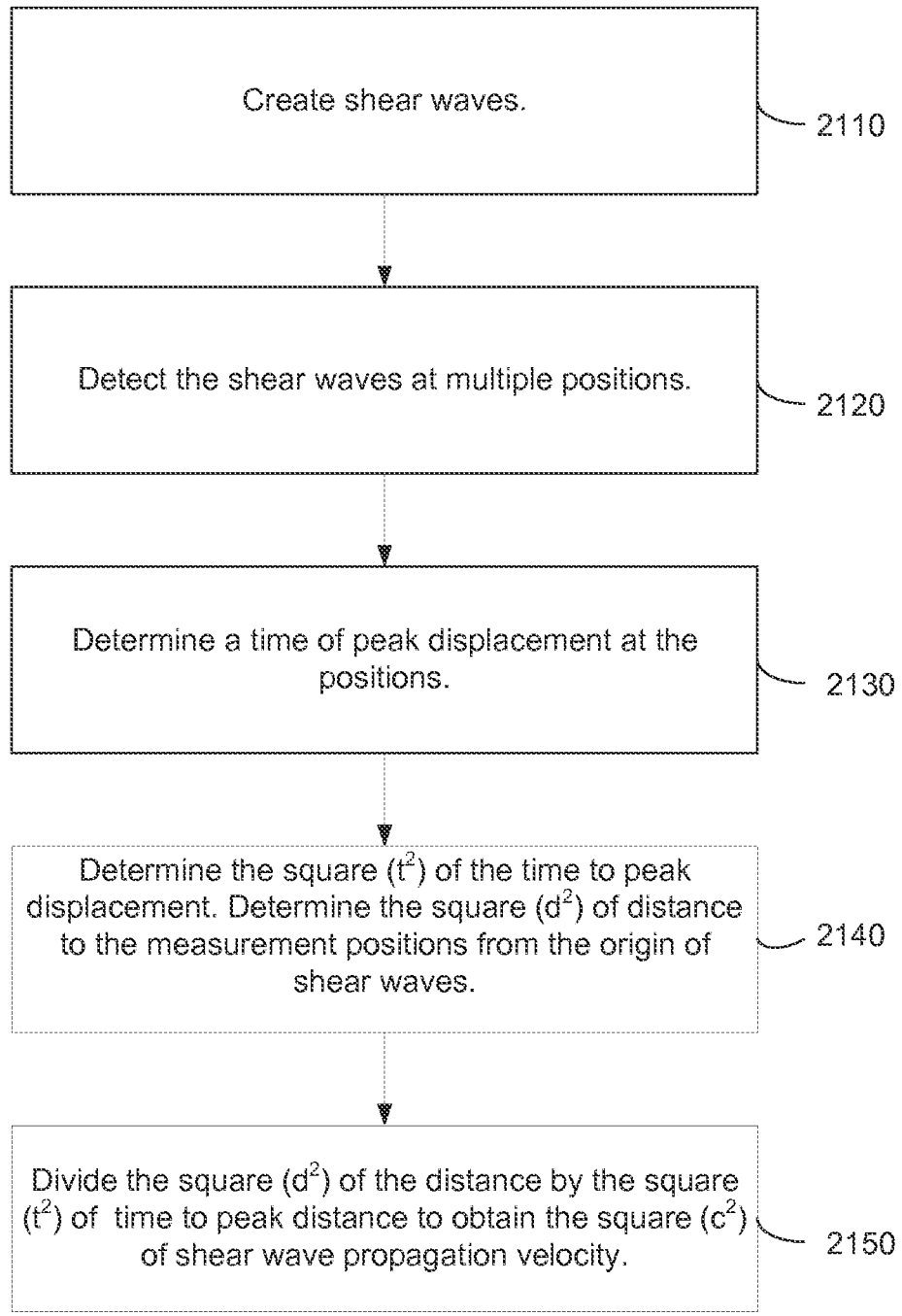
FIG. 21. Flow chart of a process according to some embodiments.

FIG. 21 is a flow chart of a process according to some embodiments. Shear waves are created at 2110. The shear waves are detected at multiple positions at 2120. A time to peak displacement is determined for each of the positions at 2130. The square $t^2$ of the time to peak displacement is determined for each of the multiple positions at 2140. The square $d^2$ of the distance to each of the measurement positions is determined at 2140. $d^2$ is divided by $t^2$ for each of the multiple positions to obtain the square $c^2$ of shear wave velocity for each of the multiple positions at 2150.

Figure 22:
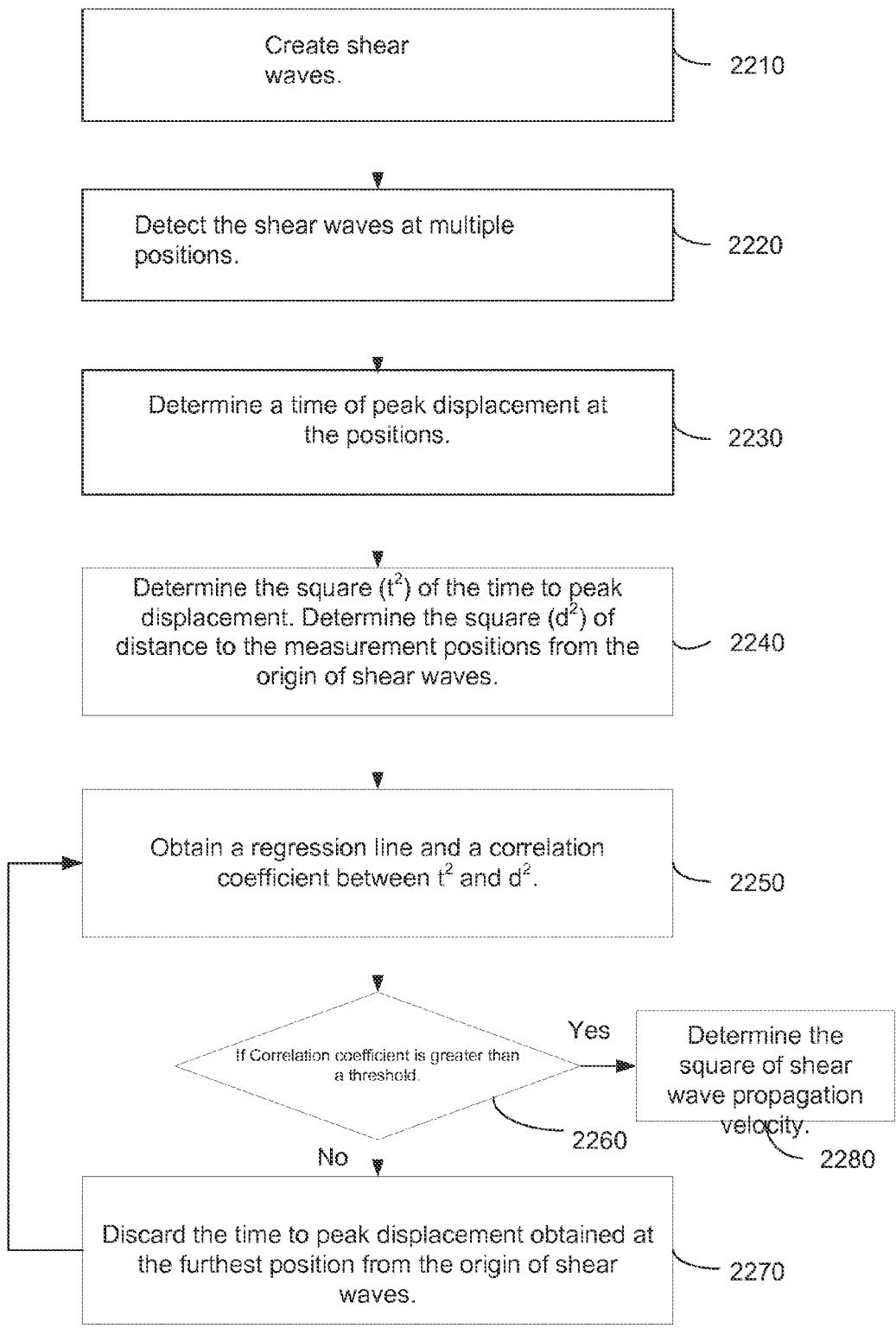
FIG. 22. Flow chart of a process according to some embodiments.

In some embodiments, shear waves are created at 2210 of the flow chart of FIG. 22. The shear waves are detected at multiple positions at 2220. A time to peak displacement is determined for each of the positions. The square $t^2$ of the time to peak displacement for each of the multiple positions is determined. The square $d^2$ of the distance to the measurement positions from the origin of shear waves is determined at 2250. A regression line and a correlation coefficient between the determined values of $t^2$ and $d^2$ are obtained at 2250. If the correlation coefficient is greater than a threshold (2260), the square $c^2$ of shear wave propagation velocity is determined by calculating a slope of the regression line at 2280. If the correlation coefficient is not greater than the threshold (2260), the time to peak displacement obtained at the furthest position from the origin of shear waves in the data set is discarded at 2270. Flow returns to 2250 to obtain a new regression line and a new correlation coefficient based on the new data set and continues as described above, which may result in discarding the time to peak displacement obtained at the next-furthest position from the origin and again returning to 2250.

In some embodiments, a measurement point near the shear wave origin, for example, the measurement point 1930, may be used as a reference position and a new calculation to obtain the square of shear wave propagation velocity may be performed as follows.

First, one of the measurement positions may be selected. Second, a distance of each of the multiple positions from the selected position is determined. A square of the distance of each of the multiple positions from the selected position is calculated. This process will be discussed in the following sections in detail. The distance $d_1$ from the shear wave origin 1910 to the measurement point 1930 is subtracted from the distance, making the new distance 0 from the selected position. The distance $d_1$ is also subtracted from the distance to each of the measurement points 1940, 1950 and 1960. Likewise, the time to peak displacement at the point 1930 (or the selected position) is also subtracted from the time to peak displacement at each of the measurement points 1930, 1940, 1950, 1960 as previously discussed. Then, the square of time to peak displacement at each of the measurement points 1930, 1940, 1950 and 1960 is calculated. Also, the square of the distance from the selected position 1930 to each of the measurement points is calculated. In some embodiments, the square of the distance to any of the measurement points will be divided by the square of time to peak displacement at the same measurement point to obtain the square of shear wave propagation velocity, as in the process in 2150.

The measurement data (for example, data at the shear wave origin 1910) acquired before the shear wave arrives at the selected position may be discarded from the data set because it is not needed for the presently-described process. In some embodiments, a regression line is determined for the new data set as previously described. The inverse of the regression line slope is obtained to yield the square of shear wave propagation velocity. In some embodiments, a regression line and a correlation coefficient are determined for the new data set as previously discussed. If the correlation coefficient is higher than a preset threshold, the inverse of the regression line slope is obtained to yield the square of shear wave propagation velocity. If the correlation coefficient is lower than the threshold, the data furthest from the selected position is discarded. Then a new regression line and a new correlation coefficient are determined. This process may be repeated until a correlation coefficient greater than the threshold is determined, after which the square of shear wave propagation velocity is determined as shown in the process in FIG. 22.

In the discussion above, the peak displacement was used to measure time of flight of a shear wave from one position to another. Other displacement properties may be used to measure the time of flight such as, for example, the leading positive slope of the displacement curves as shown in FIG. 16. The maximum temporal derivative of displacement may be also used to measure time of flight of a shear wave from one position to another.

In the discussion above, the time to peak displacement of a shear wave is determined from the onset of the shear wave generation. The time may be accurately determined from the transmission of the ultrasound pulse which creates the shear wave. In some embodiments, the time may be determined from a time at which the ultrasound pulse arrives at the focus of the pulse or the origin of shear wave. In some embodiments, the time to peak displacement of a shear wave may be determined from any point in time.

Figure 3:
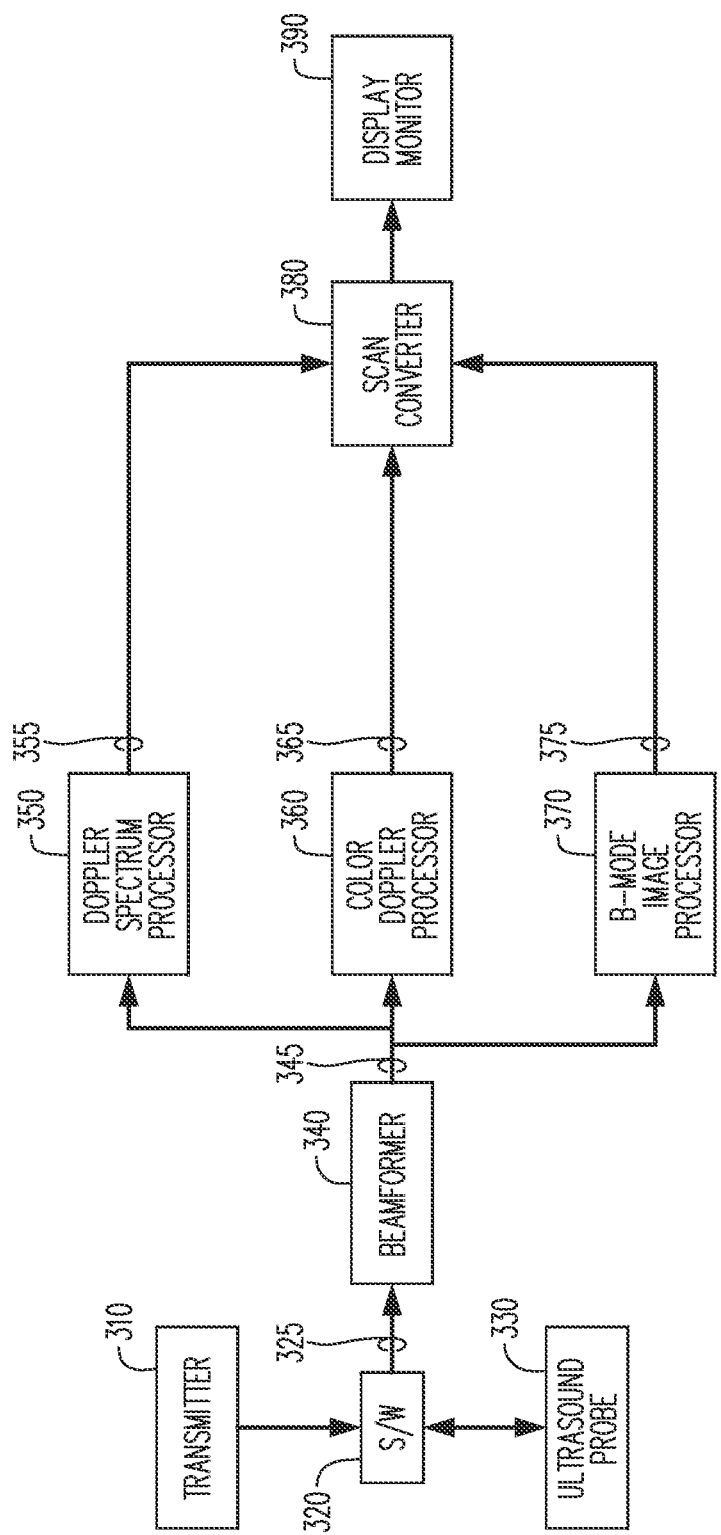
FIG. 3. A diagram of a conventional ultrasound imaging system.

FIG. 3 shows a diagram of a conventional ultrasound diagnostic imaging system with B-mode imaging, Doppler spectrum and color Doppler imaging. The system may include other imaging modes, e.g. elasticity imaging, 3D imaging, real-time 3D imaging, tissue Doppler imaging, tissue harmonic imaging, contrast imaging and others. An ultrasound signal is transmitted from an ultrasound probe 330 driven by a transmitter/transmit beamformer 310 through a transmit/receive switch 320. The probe 320 may consist of an array of ultrasound transducer elements which are separately driven by the transmitter/transmit beamformer 310 with different time-delays so that a transmit ultrasound beam is focused and steered. A receive beamformer 340 receives the received ultrasound signals from the probe 330 through the switch 320 and processes the signals 325. The receive beamformer 340 applies delays and/or phases to the signals and the resultant signals are summed for focusing and steering a received ultrasound beam. The receive beamformer 340 may also apply apodization, amplification and filtering.

The processed signal 345 is coupled to a Doppler spectrum processor 350, a color Doppler processor 360, and a B-mode image processor 370. The Doppler spectrum processor 350 includes a Doppler signal processor and a spectrum analyzer, and processes Doppler flow velocity signals and calculates and outputs a Doppler spectrum 355. The color Doppler processor 360 processes the received signal 345 and calculates and outputs velocity, power and variance signals 365. The B-mode image processor 370 processes the received signal 345 and calculates and outputs a B-mode image 375 or the amplitude of the signal by an amplitude detection.

The Doppler spectrum signals 355, color Doppler processor signals (velocity, power, and variance) 365 and B-mode processor signals 375 are coupled to a scan converter 380 that converts the signals to scan-converted signals. The output of scan converter 380 is coupled to a display monitor 390 for displaying ultrasound images.

Figure 2:
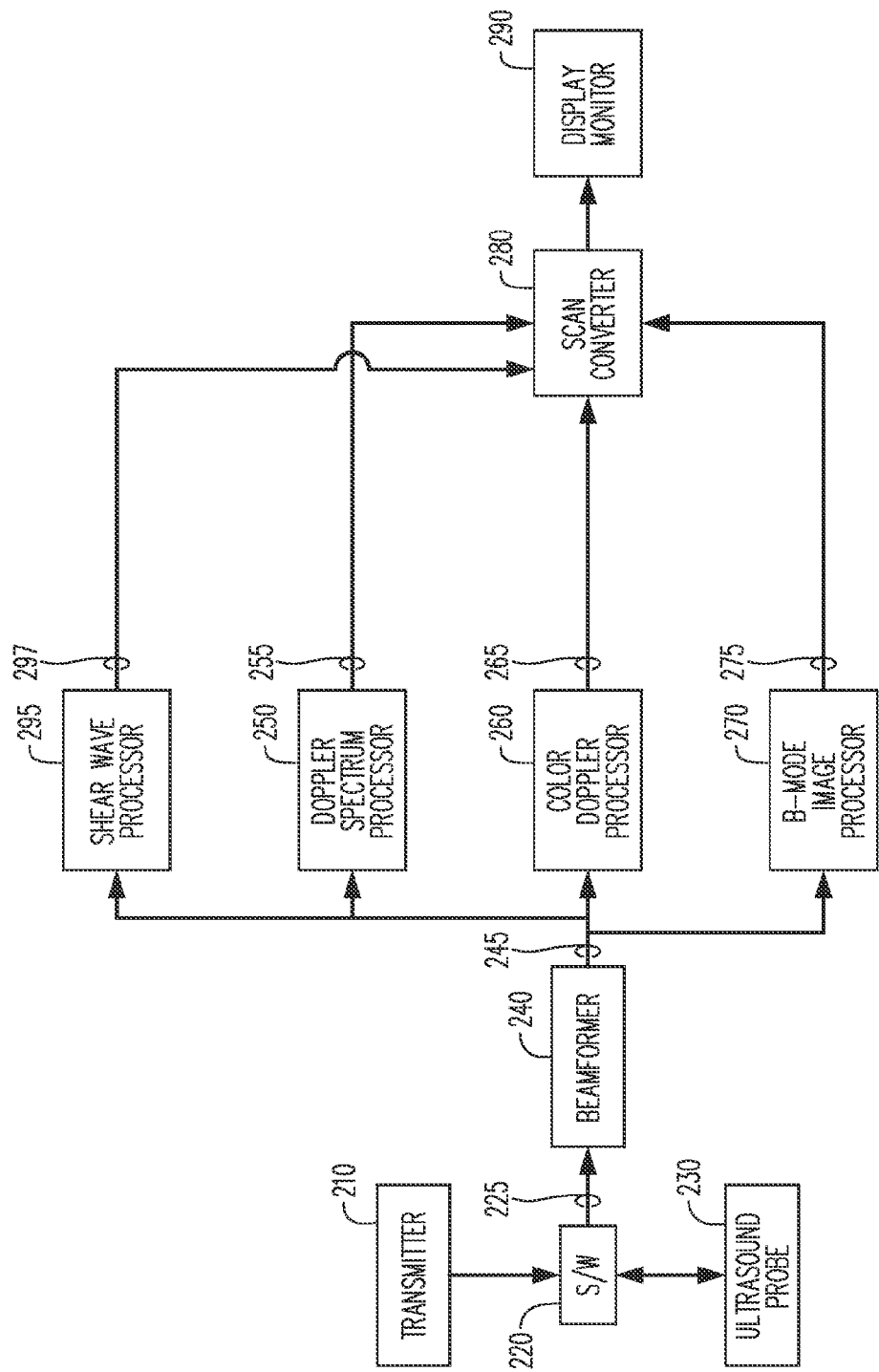
FIG. 2. A diagram of an ultrasound imaging system of some embodiments.

FIG. 2 shows a diagram of elements of an ultrasound imaging system including a shear wave processor 295 according to some embodiments. The ultrasound system in FIG. 2 transmits strong ultrasound pulses to biological tissue to create acoustic radiation forces which push the biological tissue. Shear waves are created and propagate in the tissue after the biological tissue is pushed. The ultrasound system then transmits and receives ultrasound pulses to track the shear waves as the shear waves propagate in the biological tissue. Multiple received ultrasound beams may be simultaneously formed by the receive beamformer 240. Likewise, multiple transmitted ultrasound beams may be simultaneously formed by the transmitter/transmit beamformer 210. Received ultrasound signals from the receive beamformer 240 are processed to obtain tissue displacement, Doppler velocity, correlation and shear wave propagation velocity squared as previously described. The shear wave processor 295 may perform the shear wave and strain processing methods described previously. The shear wave processor 295 receives output 245 from the receive beamformer 240. Output 297 comprises shear wave velocity squared data or other shear wave properties. For example, the shear wave processor 295 outputs the square of the shear wave propagation velocity to a scan converter 280 and a representation of the square of the shear wave propagation velocity is output to the display monitor along with the B-mode, color Doppler or spectral Doppler images.

The shear wave processor 295 may comprise of general purpose central processing units (CPUs), digital signal processors (DSPs), field programmable Arrays (FPGAs), graphic processing units (GPUs) and/or discreet electronics devices.

FIG. 2 represents a logical architecture according to some embodiments, and actual implementations may include more or different elements arranged in other manners. Other topologies may be used in conjunction with other embodiments. Moreover, each element of the FIG. 2 system may be implemented by any number of computing devices in communication with one another via any number of other public and/or private networks. Two or more of such computing devices may be located remote from one another and may communicate with one another via any known manner of network(s) and/or a dedicated connection. The system may comprise any number of hardware and/or software elements suitable to provide the functions described herein as well as any other functions. For example, any computing device used in an implementation of the FIG. 2 system may include a processor to execute program code such that the computing device operates as described herein.

All systems and processes discussed herein may be embodied in program code stored on one or more non-transitory computer-readable media. Such media may include, for example, a floppy disk, a CD-ROM, a DVD-ROM, a Blu-ray disk, a Flash drive, magnetic tape, and solid state Random Access Memory (RAM) or Read Only Memory (ROM) storage units. The program code may be executed by one or more computing devices to perform any of the processes described herein. In this regard, the one or more computing devices may also include one or more memory devices (e.g., RAM or ROM storage units) to store the program code prior to execution thereof. Embodiments are therefore not limited to any specific combination of hardware and software.

One or more embodiments have been described. Nevertheless, various modifications will be apparent to those in the art.

The invention claimed is:

1. A method comprising:
applying a first ultrasound pulse to biological tissue to create shear waves in the biological tissue;
transmitting a second ultrasound pulse into the biological tissue;
receiving one or more ultrasound signals from the biological tissue generated in response to the second ultrasound pulse;
detecting the shear waves in the biological tissue based on the received one or more ultrasound signals;
determining a time to peak displacement of the shear waves at each of multiple positions in the biological tissue;
determining a square of shear wave propagation velocity based on the determined time to peak displacement of the shear waves at each of the multiple positions;
determining a color code representing the square of shear wave propagation velocity; and
displaying an image on a display monitor in which the biological tissue is represented by a color corresponding to the color code,
wherein determining the square of shear wave propagation velocity comprises:
calculating a square of the time to peak displacement of the shear waves at each of the multiple positions;
calculating a square of a distance of each of the multiple positions from an origin of the shear waves; and
calculating a regression line and a correlation coefficient between the square of the time to peak displacement and the square of the distance from the origin of the shear waves for each of the multiple positions;
determining a plurality of the multiple positions for which the correlation coefficient between the square of the time to peak displacement and the square of the distance from the origin of the shear waves for the plurality of the multiple positions is greater than a preset threshold;
calculating a second regression line between the square of the time to peak displacement and the square of the distance from the origin of the shear waves for each of the plurality of the multiple positions; and
determining a slope of the second regression line.

2. A method according to claim 1, wherein determining the time to peak displacement of the shear waves comprises:
   calculating a cross correlation, a sum of absolute differences (SAD), a sum of square differences (SSD), a sum of absolute cubic differences (SCD), or a sum of absolute power differences (SPD) between the received ultrasound signals.

3. A method according to claim 1, wherein determining the time to peak displacement of the shear waves comprises:
   calculating a color Doppler shift frequency, a color Doppler phase or a color Doppler velocity based on the I-Q signals of the received ultrasound signals.

4. A non-transitory medium storing computer-executable program code, the program code executable by a computing device to:
   apply a first ultrasound pulse to biological tissue to create shear waves in the biological tissue;
   transmit a second ultrasound pulse into the biological tissue;
   receive one or more ultrasound signals from the biological tissue generated in response to the second ultrasound pulse;
   detect the shear waves in the biological tissue based on the received one or more ultrasound signals;
   determine a time to peak displacement of the shear waves at each of multiple positions in the biological tissue;
   determine a square of shear wave propagation velocity based on the determined time to peak displacement of the shear waves at each of the multiple positions;
   determine a color code representing the square of shear wave propagation velocity; and
   display an image on a display monitor in which the biological tissue is represented by a color corresponding to the color code,
   wherein determination of a square of shear wave propagation velocity based on the determined time to peak displacement of the shear waves at each of the multiple positions comprises:
   calculation of a square of the time to peak displacement of the shear waves at each of the multiple positions;
   calculation of a square of a distance of each of the multiple positions from an origin of the shear waves; and
   calculation of a regression line and a correlation coefficient between the square of the time to peak displacement and the square of the distance from the origin of the shear waves for each of the multiple positions;
   calculation of a square of the time to peak displacement of the shear waves at each of the multiple positions;
   calculation of a square of a distance of each of the multiple positions from an origin of the shear waves; and
   calculation of a regression line and a correlation coefficient between the square of the time to peak displacement and the square of the distance from the origin of the shear waves for each of the multiple positions.

5. A medium according to claim 4, wherein the program code executable by a computing device to determine the time to peak displacement of the shear waves comprises program code executable by a computing device to:
   calculate a cross correlation, a sum of absolute differences (SAD), a sum of square differences (SSD), a sum of absolute cubic differences (SCD), or a sum of absolute power differences (SPD) between the received ultrasound signals.

6. A medium according to claim 4, wherein the program code executable by a computing device to determine the time to peak displacement of the shear waves comprises program code executable by a computing device to:
   calculate a color Doppler shift frequency, a color Doppler phase or a color Doppler velocity based on the I-Q signals of the received ultrasound signals.

7. A system comprising:
   a memory device;
   a processor to execute computer-executable program code stored in the memory to cause the system to:
   apply a first ultrasound pulse to biological tissue to create shear waves in the biological tissue;
   transmit a second ultrasound pulse into the biological tissue;
   receive one or more ultrasound signals from the biological tissue generated in response to the second ultrasound pulse;
   detect the shear waves in the biological tissue based on the received one or more ultrasound signals;
   determine a time to peak displacement of the shear waves at each of multiple positions in the biological tissue;
   determine a square of shear wave propagation velocity based on the determined time to peak displacement of the shear waves at each of the multiple positions;
   determine a color code representing the square of shear wave propagation velocity; and
   display an image on a display monitor in which the biological tissue is represented by a color corresponding to the color code,
   wherein determination of the square of shear wave propagation velocity comprises:
   calculation of a square of the time to peak displacement of the shear waves at each of the multiple positions;
   calculation of a square of a distance of each of the multiple positions from an origin of the shear waves;
   calculation of a regression line and a correlation coefficient between the square of the time to peak displacement and the square of the distance from the origin of the shear waves for each of the multiple positions;
   calculation of a square of the time to peak displacement of the shear waves at each of the multiple positions;
   calculation of a square of a distance of each of the multiple positions from an origin of the shear waves; and
   calculation of a regression line and a correlation coefficient between the square of the time to peak displacement and the square of the distance from the origin of the shear waves for each of the multiple positions.

8. A system according to claim 7, wherein determination of the time to peak displacement of the shear waves comprises:
   calculation of cross correlation, a sum of absolute differences (SAD), a sum of square differences (SSD), a sum of absolute cubic differences (SCD), or a sum of absolute power differences (SPD) between the received ultrasound signals.

9. A system according to claim 7, wherein determination of the time to peak displacement of the shear waves comprises:
   calculation of a color Doppler shift frequency, a color Doppler phase or a color Doppler velocity based on the I-Q signals of the received ultrasound signals.

* * * * *